United States Patent [19]

Newberg et al.

[11] Patent Number: 5,296,197

[45] Date of Patent: Mar. 22, 1994

[54] AUTOMATED SAMPLE EXTRACTOR OR FEEDER/INOCULATOR FOR BIOREACTORS AND SIMILAR EQUIPMENT

[75] Inventors: Douglas A. Newberg, Annapolis; Vjekoslav Pavlin, Adelphi; Richard R. Newberg, Royal Oak; Jackson C. S. Yang, Silver Spring, all of Md.

[73] Assignees: NL Technologies, Limited, Annapolis; University of Maryland at College Park, College Park, both of Md.

[21] Appl. No.: 911,052

[22] Filed: Jul. 9, 1992

[51] Int. Cl.[5] ............... G01N 1/04; F16K 31/44; F16K 51/00
[52] U.S. Cl. ............... 422/103; 73/863.81; 73/863.82; 73/863.85; 73/863.86; 137/240; 137/241; 251/144; 251/335.3; 422/99; 422/114
[58] Field of Search ............ 422/99, 100, 103, 114; 73/863.81–863.83, 863.85–863.86; 137/240, 241; 251/144, 335.3

[56] References Cited

U.S. PATENT DOCUMENTS

| | | | |
|---|---|---|---|
| 1,831,457 | 11/1931 | Larsen | 137/241 |
| 2,041,694 | 3/1934 | Buckley | 137/340 |
| 2,844,964 | 12/1952 | Guibert | 73/863.86 |
| 3,399,695 | 9/1968 | Stehlin | 137/551 |
| 3,429,552 | 2/1969 | Huley et al. | 251/129.17 |
| 3,638,499 | 2/1972 | Saint-Andre | 73/863.86 |
| 3,929,017 | 12/1975 | Kowalski | 73/198 |
| 4,022,066 | 5/1977 | Kaune | 73/863.86 |
| 4,338,689 | 7/1982 | Zieg | 4/378 |
| 4,405,561 | 9/1983 | Neale et al. | 422/145 |
| 4,669,321 | 6/1987 | Meyer | 73/863.85 |
| 4,822,570 | 4/1989 | Lerman et al. | 422/119 |
| 4,836,236 | 6/1989 | Ladisch | 137/241 |
| 4,909,271 | 3/1990 | Canaan et al. | 137/240 |
| 5,152,500 | 10/1992 | Hoobyar et al. | 251/269 |

*Primary Examiner*—James C. Housel
*Assistant Examiner*—Robert Carpenter

[57] ABSTRACT

An apparatus can withdraw a sample from a vessel or conduit or provide a sample to this vessel or conduit. This apparatus includes a main body with an inlet passage and drain passage. The main body has a longitudinal axis with the axes of the drain passage and inlet passage being inclined relative thereto. A flexible bellows is positioned within an internal cavity of the main body. A sealing tip of the bellows is movable by a valve operating rod to close an orifice to a sample cavity within the body. A sample can be taken from the vessel or conduit, through this sample cavity and out the drain passage to a sampling device when the apparatus is used as a sampler. On the other hand, a sample can be fed through the inlet passage, sample cavity and orifice to the vessel or conduit when the apparatus is used as a feeder/inoculator. Steam, pure dry air and/or a wash medium can be provided through the inlet passage to cleanse the apparatus. Crevices and exposure to moving parts are avoided in the apparatus to prevent contamination of the sample. This apparatus can be retrofitted to existing containers or vessels and can be automatically controlled and monitored.

21 Claims, 6 Drawing Sheets

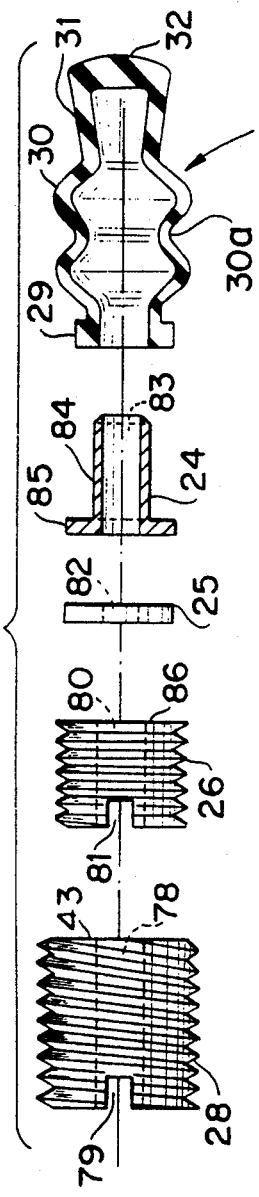

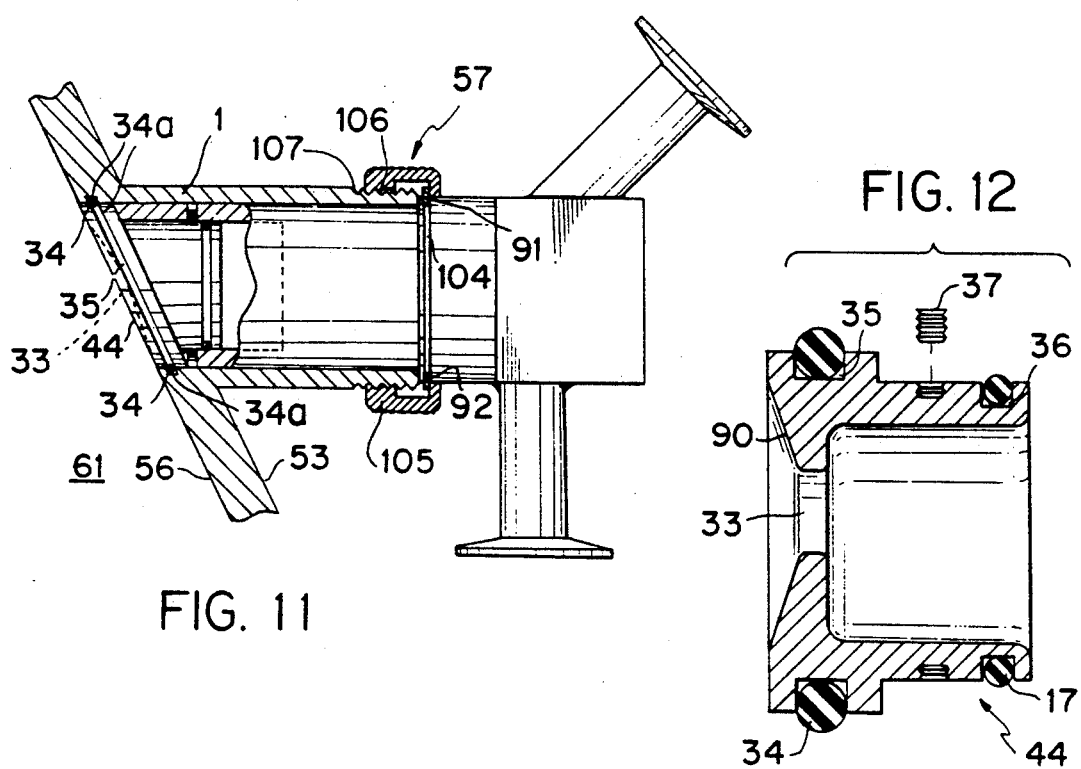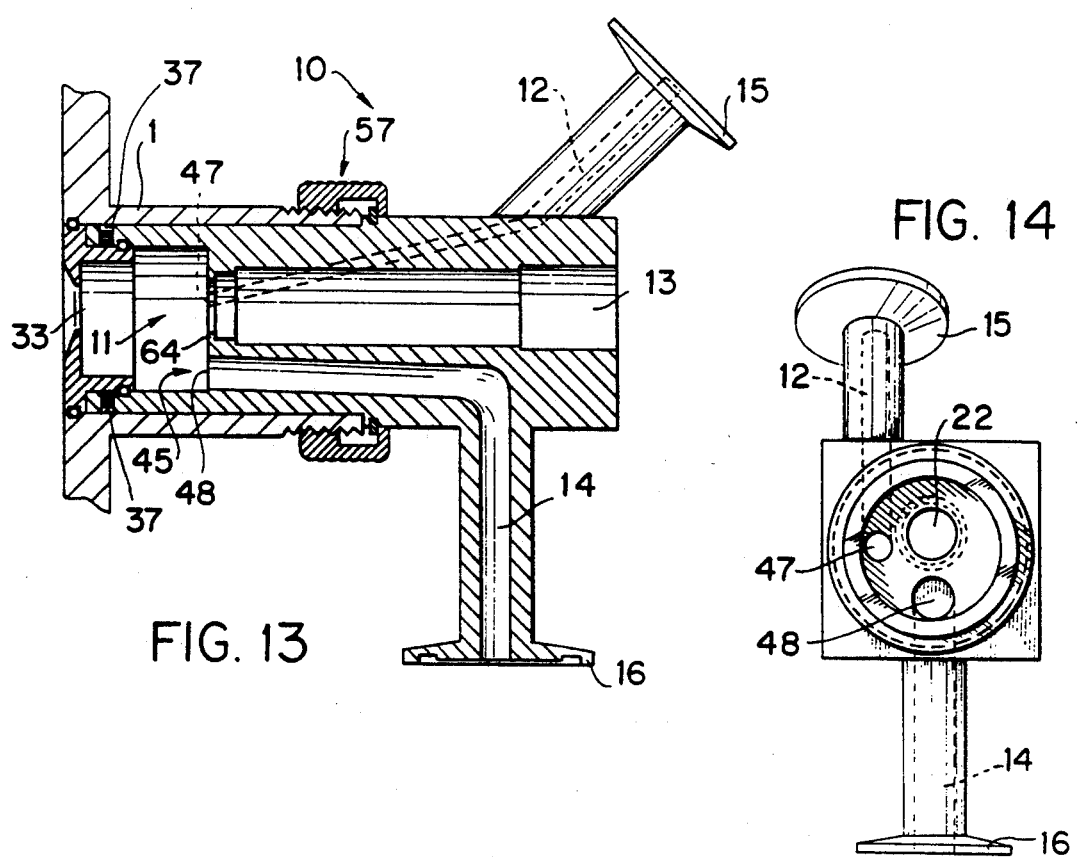

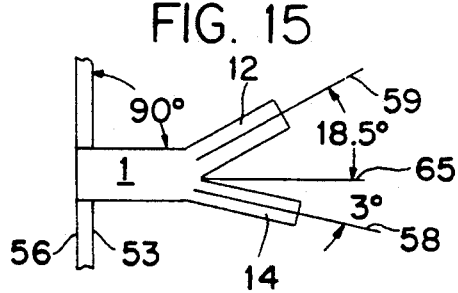
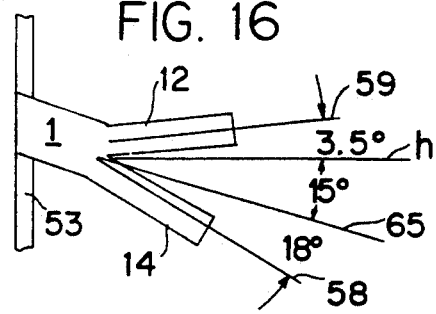
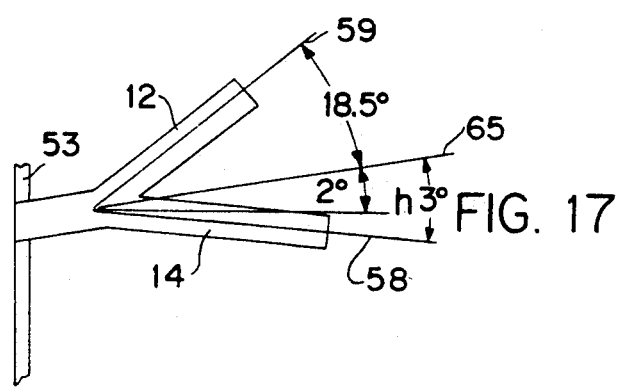
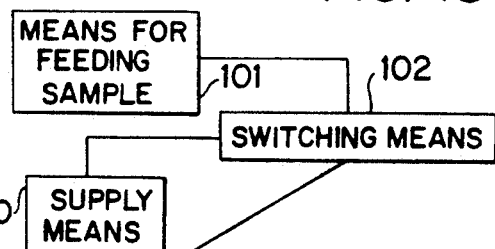
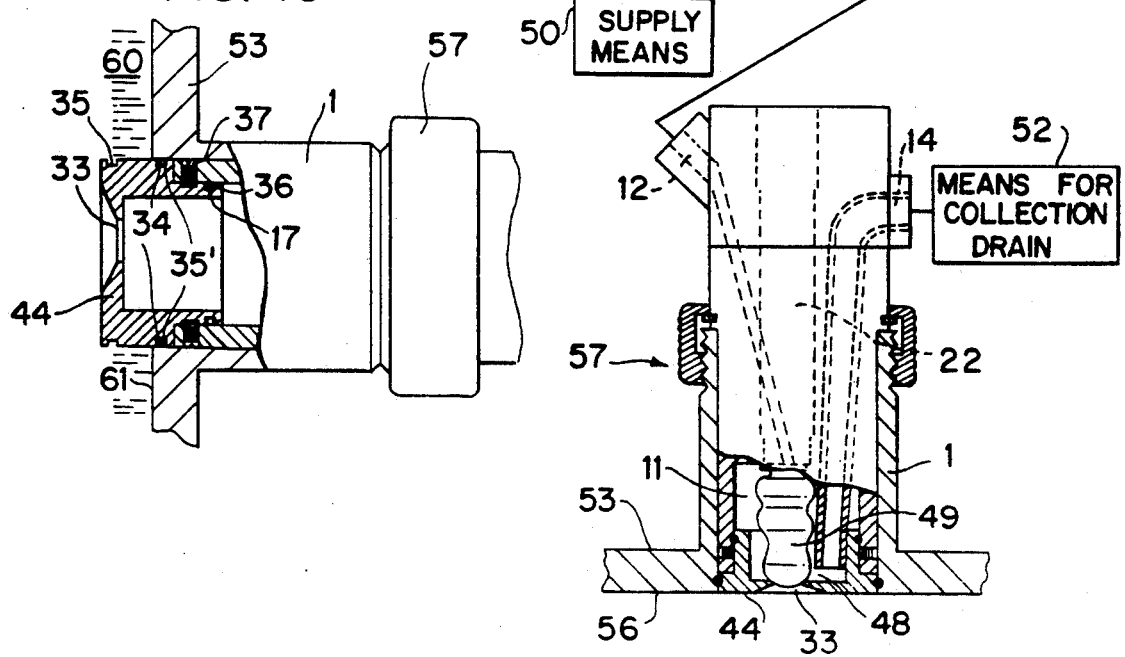

| | WAITING | STEAM | AIR | SAMPLING | AIR |
|---|---|---|---|---|---|
| SO | | | | ▓▓▓▓ | |
| V1 | | | ▓▓▓▓ | | ▓▓▓▓ |
| V2 | | ▓▓▓▓ | | | |
| V3 | | | | ▓▓▓▓ | ▓▓▓▓ |
| V4 | | ▓▓▓▓ | ▓▓▓▓ | | |
| | | V2, V4 OPEN | V1, V4 OPEN | SO, V3 OPEN | V1, V3 OPEN |

↑ 1 SEC   ↑ 1 SEC

AUTOMATED SAMPLE EXTRACTOR OR FEEDER/INOCULATOR FOR BIOREACTORS AND SIMILAR EQUIPMENT

BACKGROUND OF THE INVENTION

1. Field of the Invention

The present invention relates to an automated sample extractor or feeder/inoculator for a vessel or conduit. This vessel or conduit can be a bioreactor or other similar equipment.

2. Description of the Background Art

Development of new or more efficient commercialization of existing products requires faster and more effective methods to measure process variables. This is particularly true in processes which require cell culture and fermentation processes conducted in bioreactors where the accuracy of measurements in the research and development are critical for achieving economic production of high purity and highly refined end products.

Some factors which must be controlled include temperature and pressure. These factors are easily measured by utilizing standard sensors. However, many other factors can be measured only by removing samples for external laboratory analysis. The frequency of sample extraction for testing and measurement, number of tests on each sample and the time constraints on the process vary widely as do the methods and equipment used to obtain the samples.

In most cases, measurement processes for variables do not lend themselves to in-situ measurement by remote sensors directly in the process. Instead, samples must be physically extracted from the process and examined and manipulated outside the vessel or conduit. Before this examination and manipulation process can be effectively carried out either in a manual or automated fashion, a safe, effective means of sample extraction must be made available. This sampling process must provide a product that is an accurate subsample of the process composition.

Furthermore, since prior art designs do not lend themselves to use in existing systems, substantial modification to the system is required. The apparatus needs to minimize or eliminate the dangers associated with the sampling process in an efficient and cost effective manner while providing quality, reproducible results in order to be of value for commercial application.

One danger which must be avoided is danger to the operator or environment. When working with samples and especially hazardous samples, it is necessary to remove or feed/inoculate a sample without endangering the integrity of the process, subsequent samples, the operator or the outside environment. Many prior art devices are unsatisfactory in this area.

Also, some prior art systems are not automated. Therefore, there is potential danger posed by human procedural errors and operator and environmental exposure. Accordingly, a need exists for an automatable apparatus with the capacity for independent verification of equipment operation built in.

The materials being sampled themselves are often expensive. Therefore, excessive removal of sample should be avoided.

When taking samples, it is often important to maintain an aseptic environment. It is important that contamination from previous sampling or from the environment not contaminate the current sample or the process being sampled. Loss of a sample run or contamination of the process can have extremely expensive ramifications. Therefore, it is important to obtain a sample without the sampling procedure causing contamination.

Many prior art devices permit accumulation or pooling of samples or cleansing medium. When the device is first used this may not create a problem; however, upon subsequent runs, the samples will be contaminated or at least diluted.

Additionally in the prior art, technology used for taking samples is generally unsatisfactory for feeding/inoculating the vessel or container.

SUMMARY OF THE INVENTION

Accordingly, it is a primary object of the present invention to provide an apparatus for moving a sample of flowable material either into a vessel or conduit (an inoculation apparatus) or to move a sample of the flowable material from the vessel or conduit (a sample extractor).

It is an object of the present invention to provide an apparatus which can be retrofitted to existing standard tank port holes without other equipment modification.

Another object of the present invention is to provide an apparatus which will provide a representative subsample of the process composition.

Still another object of the present invention is to eliminate or minimize the dangers of the sampling process such as contamination of the sample, process or surrounding environment.

It is a further object of the present invention to provide an apparatus which will conduct sampling and maintain the sample in sealed arrangement such that there will be no danger to the sample itself or to the operator, the process and the surrounding environment.

Another object of the present invention is to provide an automatable system to eliminate operator error.

Yet another object of the present invention is to provide for a built-in verification of proper operation of the apparatus.

Still another object of the present invention is to provide a sample apparatus which avoids contact of the lo sample with dynamic (sliding or rotating) seals, thereby avoiding potential sites for accumulation of carryover contaminants.

A further object of the present invention is to eliminate the usual static crevice areas which may collect contaminates but yet are inaccessible to cleaning and sterilization agents and thus eliminates areas which might harbor carryover contaminants.

It is a further object of the present invention to avoid dead (stagnant) spaces in the apparatus which would result in samples that are not truly reflective of the process.

Yet another object of the present invention is to avoid obstacles or barriers to free drainage of the samples.

Still another object of the present invention is to provide a flushing arrangement for the apparatus whereby contaminants and other material will be forced from the system.

Yet a further object of the present invention is to avoid excess process void volume inside the apparatus which would result in sample volume measurement difficulties and material wastage.

Still another object of the present invention is to avoid passive "breathing" between the seals of the apparatus and the outside environment.

Another object of the present invention is to provide an apparatus which can be repeatedly cleaned and/or sterilized in place.

Yet another object of the present invention is to provide an apparatus which can easily be removed and quickly disassembled for maintenance, including replacement of worn parts.

A further object of the present invention is to provide an apparatus whose materials are compatible with the sample materials and the process.

Yet another object of the present invention is to provide a low cost apparatus which can effectively carry out sampling or inoculation.

Still another object of the present invention is to provide an apparatus which will be reliable, easy to maintain and low cost.

Another object of the present invention is to provide multiple use capability of the apparatus including feeding/inoculation as well as sampling.

These and other objects of the present invention are fulfilled by providing an apparatus for moving a sample of flowable material through a port in a wall of a vessel or conduit. Thus, this apparatus can either feed in or withdraw materials.

The apparatus comprises a body having an internal cavity and end wall with an orifice. A means is provided for coupling the body to the port in the vessel or conduit. A diaphragm valve is positioned within the internal cavity of the body. This bulbous diaphragm valve has a rubber bellows with a tubular body and a blunt sealing tip. The tip can be moved to close or open the orifice. The tubular body of the valve is spaced from the interior surfaces of the internal cavity to thereby define a sample cavity. This sample cavity is communicable with the orifice. A valve operating rod is attached to the blunt sealing tip and is moved by an appropriate drive to open and close the orifice. A drain passage leads away from the sample cavity of the body while an inlet passage leads to the sample cavity of the body. This drain passage has a longitudinal axis which is offset with regard to the longitudinal axis of the body. Similarly, the inlet passage has a longitudinal axis which is not only offset from the longitudinal axis of the body but is also offset from the longitudinal axis of the drain passage.

In one arrangement, steam, air and/or a wash medium can be supplied through the inlet passage, sample cavity and out the drain passage in order to clean the interior of the apparatus. With the tip of the valve moved to open the orifice, the sample can then be extracted from the vessel or conduit through the sample cavity and out the drain passage. This sample will be fed to a means for collecting the sample.

When the apparatus is used for feeding or inoculating, the drainage valve is closed. This diaphragm valve is retracted and the feed or inoculant is forced through the feed passage, past the diaphragm valve into the vessel or conduit.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 3 is an exploded view of some of the various parts associated with the valve;

FIG. 4 is an end view of the rear valve operating nut shown in FIG. 3;

FIG. 5 is an end view of the front valve operating nut shown in FIG. 3;

FIG. 6 is an end view of the washer shown in FIG. 3;

FIG. 7 is an end view of the bushing shown in FIG. 3;

FIG. 8 is an exploded side view of the valve operating rod and valve operating rod cap;

FIG. 9 is an end view of the valve operating rod;

FIG. 10 is an end view of the valve operating rod cap;

FIG. 11 is a side view of the apparatus of the instant invention showing the means for coupling the apparatus to a ferrule of an apparatus or conduit;

FIG. 12 is a side, sectional view showing the cap of the body;

FIG. 13 is a side, sectional view illustrating the positioning of the inlet passage and drain passage of the apparatus of the present invention;

FIG. 14 is a schematic end view similar to FIG. 13 showing the inlet passage and outlet passage;

FIG. 15 is a schematic view of the present invention attached to a generally horizontal ferrule;

FIG. 16 is a schematic view of the instant invention showing the apparatus connected to a downwardly sloping ferrule;

FIG. 17 is a schematic view of the instant invention showing the apparatus attached to an upwardly sloping ferrule;

FIG. 18 is a schematic view of the instant apparatus used as a feeder/inoculator;

FIG. 19 is a view similar to FIG. 13 showing the apparatus extending beyond the interior wall of the vessel or conduit;

DETAILED DESCRIPTION OF THE PREFERRED EMBODIMENTS

Figure 1:
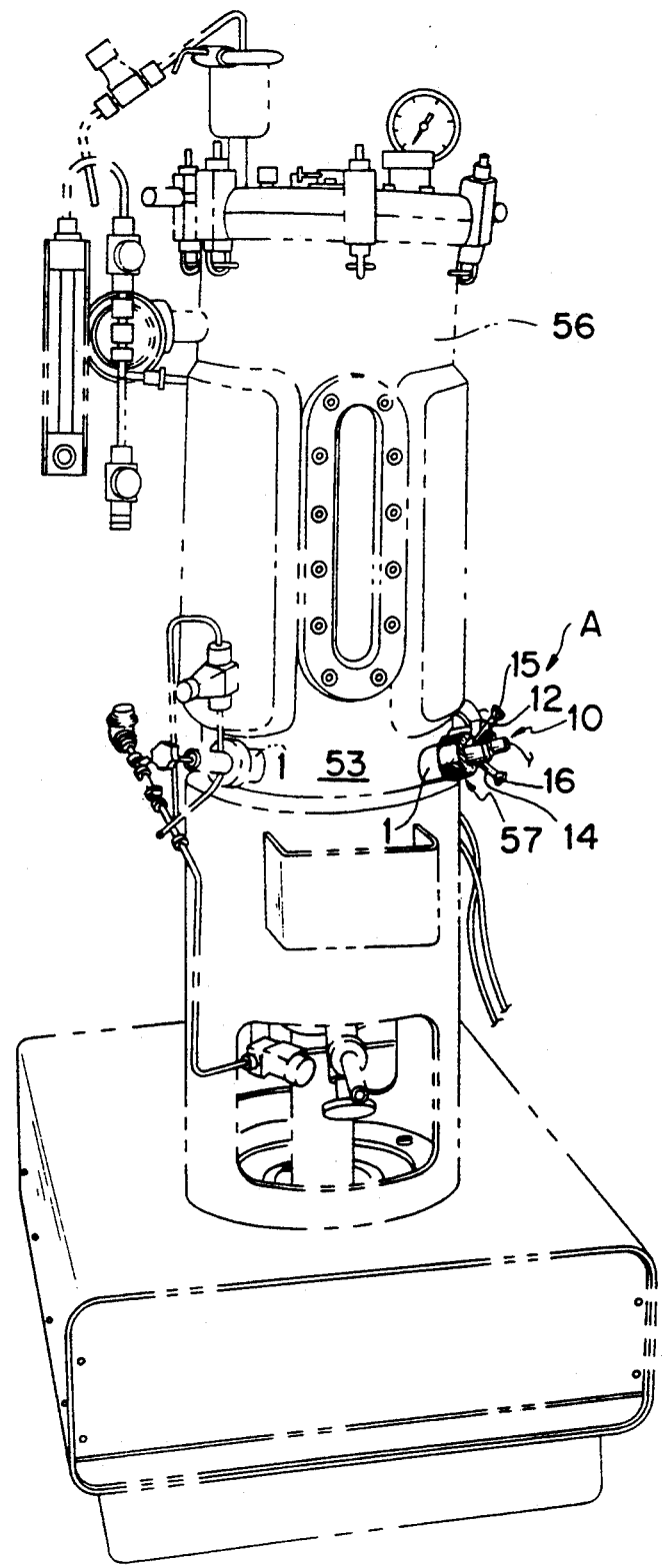
FIG. 1 is a perspective view showing the apparatus of the present invention attached to a vessel.

Referring in detail to the drawings and with particular reference to FIG. 1, a vessel 53 to which the instant apparatus A will be attached is shown. It should be appreciated that the instant invention can be attached to a vessel with a static charge or to a conduit with a static or movable charge. Because this vessel of FIG. 1 is not a part of the instant invention, it is shown in dotted lines. As will be discussed below, this apparatus A can be mounted on the top, side or bottom of the vessel or conduit.

The vessel 53 has a ferrule 1 on the side thereof. Conventional ferrules 1 have a 25 mm internal diameter, for example. A main body 10 of the instant apparatus A has been designed to have an outer diameter generally equal to or slightly less than a standard ferrule diameter. While this 25 mm dimension has been given, it should be recognized that it is merely necessary to have the outer diameter of the body 10 of the instant apparatus A slightly less than the inner diameter of any existing size ferrule. The instant apparatus A of any size can therefore be easily retrofit to existing vessels or conduits with ports of any size. Of course, the instant apparatus can also be assembled to newly manufactured vessels or conduits.

The necessary equipment for either charging a sample to the vessel or conduit 53 or removing a sample from the vessel or conduit 53 is provided through body 10 of the instant apparatus. Therefore, it is not necessary to alter existing equipment when using the instant invention. This arrangement provides for easy retrofit with standard designed vessels or conduits.

Figure 2:
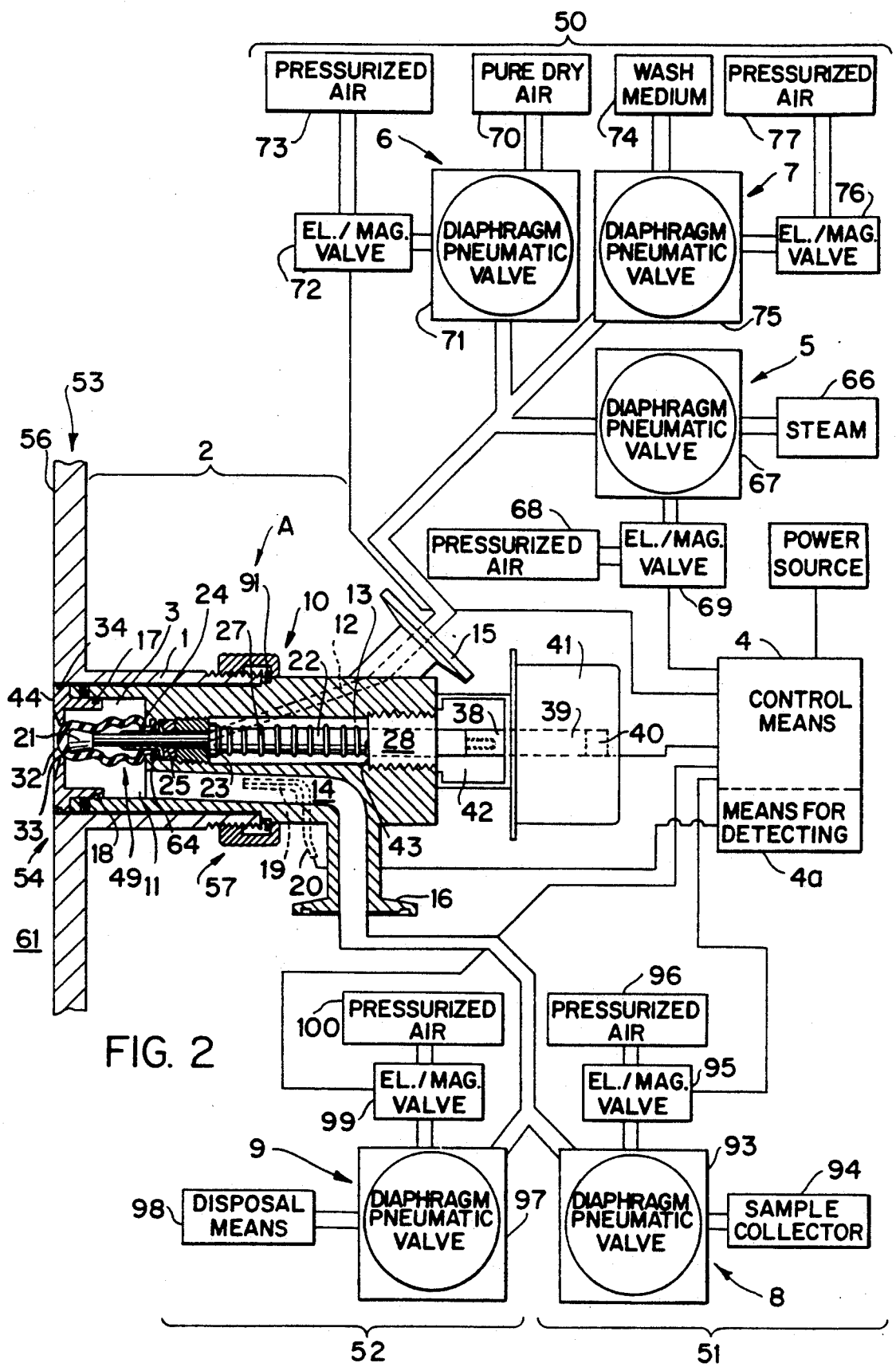
FIG. 2 is a schematic view of the apparatus of the present invention used as an extractor.

Turning now to FIG. 2, the instant apparatus A will be described in more detail. A main sample subassembly 2 is shown. This subassembly can be machined from a single piece of metal (plastic or other material) thereby being a single, one-piece, unitary structure. Thereby, the need for several additional junctions is eliminated with the instant apparatus. Each such junction would represent a potential point for contamination and malfunction. Due to the unique sealing arrangement of the instant invention, however, it is not mandatory to use a main sample subassembly machined from a single piece of metal or other material. For example, the subassembly can be permanently affixed (welded, glued, etc.) into a single unit functioning essentially as one piece.

The main sample subassembly 2 comprises a body 10 with an internal cavity 3. This cavity 3 includes a sample cavity 11 and a central bore 13 which will be discussed in more detail below.

Connected to the apparatus A of the instant invention is a control means 4. This means can be a programmable logic controller, computer operated controller or the like. A part of the control means includes a means for detecting 4a. The operation of this control means 4 and the means for detecting 4a will be described in more detail below.

A supply means 50 is provided for supplying at least one of steam, air and wash medium to the apparatus. This supply means 50 helps maintain an aseptic environment. In some situations, steam alone is sufficient for cleansing the system. In other uses, it is necessary to use pure dry air or a wash medium. Moreover, any combination of these materials can be used. The wash medium can include detergents, alcohol, an alkaline rinse, acid rinse or other wash material. It should be evident that many different arrangements can be used for cleaning and/or sterilizing the instant invention.

The supply means 50 of the instant invention includes a steam feed valve block 5, a pure dry air valve block 6 and a wash medium valve block 7. The steam feed valve block 5 includes a steam source 66 connected to a diaphragm pneumatic valve 67. Also connected to this valve 67 through an electromagnetic valve 69 is a pressurized air source 68. It should be noted that any suitable type of automatic or manual valves 67 and 69 can be used in the instant invention or that these two valves can be combined into a single unit.

The pure dry air valve block 6 includes a pure dry air source 70. This pure dry air source 70 is connected to a diaphragm pneumatic valve 71. Also connected to this valve 71 through an electromagnetic valve 72 is a source of pressurized air 73. Similarly to valves 67 and 69, it should be understood that any type of valve can be used for the valves 71, 72. Also, a single unit could replace these two valves 71, 72.

The wash medium valve block 7 includes a supply of wash medium 74. As noted above, this wash medium can be a detergent wash, an alkaline wash, an acid wash, an alcohol wash or any suitable cleansing arrangement. The supply for wash medium 74 is connected to a diaphragm pneumatic valve 75. Again, similarly to valve 67, 69, 71 and 72, any suitable valve or a single unit can be used for these valves 75 and 76.

The electromagnetic valves 69, 72 and 76 are indicated as being connected to the control means 4. It should be noted that the diaphragm pneumatic valves 67, 71 and 75 are also connected to the control means 4. It is merely necessary for the control means 4 to control supply of pressurized air, steam, pure dry air and/or wash medium to the inlet passage 12. Each of these mediums is connected to the inlet passage 12 through the respective valves 67, 71 and 75. Moreover, while three valve blocks 5, 6 and 7 are shown, any of these can be omitted or additional valve blocks could be used as needed. Also, valves 69, 72 and 76 can be combined into a single valve.

The inlet passage 12 is shown as being continuous from the main sample subassembly 2 to the supply means 50. As noted above, this main sample subassembly can be machined from a single block. Appropriate tubing, piping or other connectors can be used to connect the inlet passage 12 bored within the main sample subassembly 2 to the supply means 50. A tri-clamp connection 15 connects this tubing or piping to the inlet passage within the main sample subassembly.

A drain passage 14 is also provided in the instant invention. This drain passage can be bored within the main sample subassembly 2 or can be piping connected to a downstream means for collecting a sample 51 and means for collecting drain 52. These means 51 and 52 will be discussed in more detail below. Similarly to the connection for the inlet passage at 15, the drain passage 14 has connection 16. Rather than using a tri-clamp at the connections 15 and 16, any suitable connection arrangement can be made.

Both the inlet passage 12 and drain passage 14 are connected to the interior sample cavity 11 of body 10. This body 10 not only includes sample cavity 11 but a central bore 13 which together form the above-noted internal cavity 3.

Extending through the central bore 13 is a valve operating rod 22. This valve operating rod 22 is connected to a pin 38 at one end thereof. This pin 38 serves as a manual override lever which will be discussed in more detail below. The pin 38 is exposed at area 42 such that an operator can grasp the connector pin 38. The pin 38 connects the valve operating rod 22 to an actuator piston 39 of an electromagnetic actuator 40. The electromagnetic actuator 40 is positioned within housing 41.

The electromagnetic actuator 40 is controlled by the control means 4. This control means 4 can cause movement of the valve operating rod 22 by actuating the electromagnetic actuator 40 in order to reciprocate the valve operating rod 22 in the central bore 13. If, for some reason, the control means should fail, an operator can simply grasp the connector pin 38 through the exposed area 42 and then manually reciprocate the valve operating rod 22.

Apart from electromagnetic actuator 40, it is possible to use a less expensive design for opening/closing the valve. For example, an electric or pneumatic solenoid mechanism can be used. Also, other than grasping the rod 22 at connector pin 38, it would be possible to grasp the lower end of a rod 63 extending through housing 41, for example. As a safety precaution, some portion of the actuator or rod merely needs to be accessible to an operator such that manual operation can be carried out.

The valve operating rod extends through a rear valve operating nut/bearing 28 and a front valve operating nut/bearing 26. Both of these nuts 28, 26 are positioned within the central bore 13. While nuts 28 and 26 are shown, it should be appreciated that any appropriate arrangement can be used for mounting the valve operating rod 22 in the body 10. By using such nuts 28, 26, however, assembly and disassembly of the sample subassembly 2 can be easily carried out.

Extending between seat 43 of the rear valve operating nut 28 and the valve operating rod detent 23 is a spring 27. This spring 27 will urge the operating rod 22 away from the actuator 41. This will cause blunt sealing tip 32 of bellows 30 to close the orifice 33 as will be discussed in more detail below. By urging the tip 32 in this direction, the instant apparatus will automatically close orifice 33 upon a power failure. Thus, fail safe operation of the instant apparatus can be ensured.

Turning to FIG. 3, the rear valve operating nut 28, front valve operating nut 26, washer 25, bushing 24 and bellows 30 are shown. The diaphragm valve 49 includes the bellows 30 as well as the valve operating rod cap 21, rod 22, bushing 24 and washer 25. In FIGS. 3 and 4, the rear valve operating nut 28 is shown. The seat 43 for the spring 27 is indicated in this FIG. 3. Also, a central bore 78 through the rear valve operating nut 28 is shown. The valve operating rod 22 will extend through this bore 78. A transverse groove 79 for tightening of nut 28 is also shown in these figures.

In FIGS. 3 and 5, the front valve operating nut 26 is shown. Similarly to the rear valve operating nut 28, this front valve operating nut 26 includes a central bore 80 and a transverse groove 81.

A washer 25 and bushing 24 are shown in FIGS. 3, 6 and 7. The washer 25 has a central bore 82 while the bushing 24 has a central bore 83. The bushing 24 is divided into a neck 84 and base 85. Finally, FIG. 3 shows the bellows 30 of the diaphragm valve 49. The folds 30 of the bellows are sufficiently spaced such that material will not become entrained therein.

The base 29 of the bellows 30 is compressed against the neck 84 of the bushing 24. This neck 84 will push the base 29 against an inner, annular side of lip 64 of body 10 adjacent the central bore 13. This force helps hold the diaphragm base immobile and forms a seal preventing entrance of the sample, steam, air and/or wash medium into the central bore. Pressure on the bushing 24 is produced by tightening the front push rod nut 26 on the central bore 13. The washer 25 between the bushing base 84 and nut 26 isolates the bushing 24 (and the base 29 of bellows 30) from the torque produced when the nut is tightened.

At the other end of bellows 30, the bulb shape of the blunt sealing tip 32 will avoid dead space (stagnation area) at the sampling orifice 33. Of course this blunt sealing tip 32 can be configured in many ways. It is merely necessary that an appropriate seal be formed with the orifice.

Returning to FIG. 2, the alignment of the components shown in FIG. 3 can be seen. The valve operating rod 22 extends through the rear valve operating nut 28, front valve operating nut 26, washer 25, bushing 24 and into the bellows 30. The washer 25 is in engagement with the base 85 of the bushing 24 and one end 86 of the front valve operating nut 26.

The neck 84 of the bushing 24 provides for a tight support for the bellows 30. The bellows seen in FIGS. 2 and 3 is shown with a plurality of folds 30a. However, the end of the bellows 30 away from orifice 33 is shown as being flat. This is due to the neck portion 84 of the bushing 24.

The use of bellows 30 has several benefits. First, all of the moving mechanical parts (such as the valve operating rod 22 and the like) are removed from the sample in sample cavity The bellows 30 is made from a biocompatible plastic thermal or chemical tolerant material. This bellows is flexible and has a wide range of motion. This great range of motion allows the apparatus to achieve flush mounting (or penetration as shown in FIG. 19) of a vessel or conduit in a retrofit design. Further, this design allows the blunt sealing tip 32 to be withdrawn from the sampling orifice 33 over a great distance. This facet allows the apparatus to provide minimal sample size bias for samples with particles up to six mm size in this particular configuration.

As seen in FIGS. 8, 9 and 10, a portion of the valve operating rod 22 and valve operating rod cap 21 are shown. The end of this valve rod 22 has threaded screws 87 to mate with threads 88 in cap 21. Therefore, cap 21 can be screwed onto the valve operating rod 21. Of course, other connection arrangements can be made. The previously noted spring 27 will engage the detent 23 of rod 22. A lower end of the valve operating rod 22 is shown in FIG. 9. The threaded end 63 of the valve operating rod 22 will engage actuator piston 39 of actuator 40. Of course, connections other than threaded connections are possible.

A bottom view of the valve operating rod and a top view for the valve operating rod cap 21 are shown in FIGS. 9 and 10, respectively. This valve operating cap 21 and a portion of the valve operating rod 22 will be inserted into the bellows 30. This ca 21 ensures that the blunt sealing tip 32 will assuredly seal orifice 33 and not deform and protrude through the orifice 33. Also, this cap 21 will prevent tip 32 from sticking to the area around the orifice 33 when the operating rod 22 is retracted. As FIG. 8 shows, the cap 21 is enlarged such that when it is within bellows 30, it will act to also pull the sealing tip 32 away from the orifice 33 in cap 44.

The orifice 33 is provided in cap 44 for body 10 as seen in FIGS. 2 and 12. The end of body 10 has set screws 37 for affixing the cap 44 on body 10. It is contemplated that three set screws 37 are inserted through the end of body 10 and into cap 44 to hold the cap in position. The treads on each set screw must terminate before completely penetrating the cap 44 or can extend partially into cap 44 as seen in FIG. 12. The ends of set screws 37 can be flat or slightly bowed to prevent damage to cap 44. The three set screws 37 are nonequally spaced around the circumference of the cap 44. In this manner, the cap 44 must be properly oriented before the set screws 37 can be inserted. This key effect ensures proper positioning of the cap 44 such that the noncentered orifice 33 will be properly aligned with the blunt sealing tip 32 of bellows 30 when the cap 44 is mounted to body 10.

Of course, other sealing arrangements such as a bayonet or bolt and pin connection can be made. Also, the cap 44 can be screwed into body 10. However, this design has the drawback that incomplete screwing of the cap 44 onto body 10 would result in improper alignment of the blunt sealing tip 32 of bellows 30 with orifice 33. Also, the rotational movement of the cap 44 during screw mounting to body 10 can cause rubbing between the cap 44 and tip 32 of bellows 30 which might damage this tip. Therefore, the use of set screws or bolts is preferred over the design wherein the cap is screwed directly onto body 10. As another alternative, the cap 44 and body 10 can be machined from a single piece of metal, plastic or other material.

The orifice 33 of cap 44 is formed at the forward end thereof. The orifice 33 is offset from the center of cap 44 such that the blunt sealing tip 32 will be aligned therewith. The annular side 90 of cap 44 is in contact with the interior 61 of the vessel or conduit 53. Although shown slightly recessed, the sealing point of the cap 44 with the tip 32 can be substantially flush with the inner face of the wall 56 of the vessel or conduit 53. It is merely necessary for the cap 44 to have sufficient structural strength to withstand the sealing pressure of the tip 32. The closer this sealing point of cap 44 is to the inner wall 56 of the vessel or conduit 53, there is a lesser potential for development of a stagnation region.

An o-ring groove 35 is provided in cap 44 for receiving an o-ring 34 as seen in FIGS. 2, 11 and 12. A similar groove 34a is provided in the wall of the vessel or conduit 53 for receiving the o-ring 34. Depending on the vessel or conduit 53 used, this groove 34a can be omitted. The o-ring 34 in groove 35 is capable of forming a seal either against the flat surface of the vessel or conduit 53 or against a groove 34a provided therein.

On an inward side of cap 44 is another groove 36 for receiving an o-ring 17. The body 10 has a similar o-ring groove 18 for receiving this o-ring 17 as seen in FIG. 2. Of course, this groove 18 can be omitted. An adequate seal can be formed with or without such a groove 18. Due to the provision of the two o-rings 17 and 34, a proper seal can be maintained between the sample cavity 11 and the interior 56 of the vessel or conduit 53. In other words, the sample will only flow through orifice 33. The o-ring 17 prevents any process material from getting into the threaded junction 37 where the cap connects to the main body 10.

The use of these o-rings 34 and 17 provides insurance against leakage to the outside and minimizes the potential for "breathing" due to the creation of excessive pressure or vacuum buildup in the critical areas around the connection of the cap 44 to body 10 and the connection of body 10 within ferrule 1.

Additional grooves and o-rings can be provided as necessary. Sufficient seals should be provided such that leaking, contamination or passive "breathing" is avoided between the seals as noted above. Due to the sealing arrangement, the sample, steam, wash medium or the like will not leak between the cap 44 and body 10 where subsequent samples might be contaminated due to this material leaking back into the sample cavity 11 upon a change of pressure.

Also shown in FIGS. 2 and 11 is a means 57 for coupling the body 10 to the ferrule 1. This screw type means shown in FIG. 11 is merely one example for connecting the apparatus A of the instant invention to the vessel or conduit 53. A front side 91 of body 10 engages a rear side of the means for coupling 57. This means for coupling 57 will hold the body 10 against the ferrule 1 when screwed into position.

The means for coupling 57 includes a retaining ring 92 received in an annular recess 104 in body 10. The ring 92 engages a forward side of this recess 104 preventing forward movement of ring 92. The ring 92 will be proximate to the front side 91 of body 10. It should be noted that this body 10 extends beyond the side 91 and to the cap 44. Alternatively, as noted above, the cap 44 can be made integrally with the body 10 such that the body 10 would actually extend into contact with the sample in vessel or conduit 53. For simplicity's sake, however, this side 91 has merely been referred to as the front side because it faces the vessel or conduit 53.

The retaining ring 92 engages a coupler 105. This coupler 105 has a front end with threads 106 engaging screws 107 on the outside of ferrule 1. By screwing coupler 105, the body 10 can be mounted on this ferrule. As noted above, it should be appreciated that many other connecting arrangements can be provided for mounting body 10 to ferrule 1.

In the arrangement shown in FIG. 11, the wall 56 of the vessel or conduit is shown as being slanted. It should be appreciated that many different configurations for the vessel are also possible. The forward end of the body 10 and/or cap 44 can be appropriately sloped in order to mate with the interior face of the wall 56.

Returning to FIG. 2, a probe 20 is indicated within a probe orifice 19 of the drain passage 14. This probe 20 and orifice 19 can alternatively be located in the sample cavity 11 or alternatively within both the drain passage 14 and sample cavity The probe 20 can be a temperature and/or pressure probe. This probe 20 is operatively connected to the means for detecting 4a of the control means 4.

The means for detecting 4a and probe 20 can provide for independent verification of the various aspects of the system's operation. By comparing a profile of a sampling system temperature or pressure when the system is operating correctly with profiles when various components of the system fail, a determination can be made by the means for detecting 4a of a system failure (abnormal operation). Moreover, a determination can be made by the system as to the severity of the failure and whether to abort further sampling cycles as well as to sound an alarm. The temperature or pressure profile is captured from the probe 20 and fed to the means for detecting 4a. Accordingly, if the bellows 30, for example, were to rupture, the probe 20 could determine this condition. Moreover, if there was blockage in the inlet passage 12, this condition could be detected. The means for detecting 4a with the control means 4 can initiate appropriate action. This probe 20 can also detect if an adequate steam temperature has been reached during the sterilization cycle.

Downstream from the drain passage 14 is a means for collecting a sample 51 and a means for collecting drain 52. The means for collecting a sample 51 includes sample drain valve block 8. This valve block 8 has a diaphragm pneumatic valve 93 connected to the sample collector 94. This sample collector can be a sample vial subassembly, for example. Also connected to the diaphragm pneumatic valve 93 is an electromagnetic valve 95 with a pressurized air source 96.

The drain valve block 9 includes a diaphragm pneumatic valve 97 connected to a disposal means 98. Also connected to the diaphragm pneumatic valve 97 is an electromagnetic valve 99 and a source 100 of pressurized air. Similarly to the valves 67, 71 and 75, the diaphragm pneumatic valves 93 and 97 can be replaced by any known valves. Likewise, the valves 95 and 99 could also be replaced by other valves or the valves 93 and 95 and the valves 97 and 99 could be combined into a single unit. The electromagnetic valves 95 and 99 are operatively connected to the control means 4 as indicated in FIG. 2.

Turning now to FIGS. 13 and 14, the configuration for the inlet passage 12 and drain passage 14 will be described. To one side of the central bore 13 for the valve operating rod 22 is the inlet passage 12. This inlet passage declines towards the sample cavity 11. The interior surface of the sample cavity 11 is generally flat. Mounted flush with this interior surface is the opening 48 for the drain passage 14. This drain passage 14 inclines downwardly away from the sample cavity 11. In FIG. 14, the cap 44 has been omitted. It should be appreciated that the offset orifice 33 of cap 44 will be aligned with the blunt sealing tip 32 of bellows 30 (not shown) positioned on valve operating rod 22.

As can be seen in FIG. 13, the angle of inclination for the drain passage 14 is less than the angle of inclination for the inlet passage 12. Of course this relationship of the angles between the drain passage 14 and inlet passage 12 can vary. For example, a greater angle between the drain passage 14 and axis of the body can be provided than between the inlet passage 12 and the axis of body 10.

Due to the positioning of the inlet passage 12 above the drain passage 14 as well as the flush mounting of the drain passage 14 with the bottom wall of the sample cavity 11, a means 45 for preventing accumulation is formed. This means will enable free flow of the sample from the sample cavity 11 to the drain passage 14. Pooling of the sample will be avoided. Therefore, possible contamination of subsequent samples is avoided.

Also drain passage 14 has an internal diameter of 6 mm. This is generally larger than the biggest sample particle drawn from vessel 53. In that way, clogging of the drain passage 14 is avoided.

As seen in FIG. 14, due to the offset mounting of the central bore 13 having valve operating rod 22, inlet passage 12 and outlet passage 14, it is possible to squeeze each of these items within the 25 mm constraint for the outer diameter of body 10. In this manner, the body 10 can be retrofit into an existing apparatus. As noted above, the inner diameter of ferrule 1 is typically 25 mm in many devices. While this dimension can change, it should be understood that the instant invention can be inserted into existing equipment without the need for retrofitting this equipment. Of course, when larger or smaller ferrule ports exist, the instant invention can be made larger or smaller to accommodate these ferrules with correspondingly larger or smaller components.

In FIGS. 15-17, mounting of the apparatus of the instant invention is schematically represented. If the instant apparatus is to be mounted in a horizontally oriented ferrule 1 as shown in FIG. 15, the longitudinal axis 65 of the body 10 will be generally horizontal. The longitudinal axis 59 for the inlet passage 12 will be offset from axis 65 by an angle of approximately 18.5°. The longitudinal axis 58 for the drain passage 14 will be offset from the longitudinal axis 65 of the body by approximately 3°. Therefore, the slope for the inlet passage 12 is greater than the slope for the drain passage 14. This helps to ensure proper drainage of the sample, steam, air, wash medium and/or condensate.

As shown in FIG. 16, if the ferrule 1 is sloped downwardly, for example, by 15° from the horizontal plane h, the longitudinal axis 65 of the body 10 will similarly be offset by 15°. Such a downward slope of 15° is a standard design for some ports in vessels or conduits 53. With this downward inclination, the longitudinal axis 58 of the drain 14 will be offset about 18° from the horizontal plane h. The longitudinal axis 59 of the inlet passage 12 will continue to have a downward slope. This axis 59 will be offset from the horizontal plane h by approximately 3.5°. Therefore, with a downwardly oriented ferrule 1, proper flow can continue to be had with the instant invention. Pooling of the sample and steam, air, wash medium and/or condensate can be avoided in this arrangement.

In the upwardly inclined ferrule 1 of FIG. 17, the longitudinal axis 58 of the drain would have less of a slope than the longitudinal axis 59 of the inlet passage 12. Nonetheless, this arrangement continues to urge material through the system.

Process control for the instant invention for the instant invention is carried out under the direction of the control means 4. As noted above, this control means 4 can be a programmable logic controller, computer operated controller or any other suitable control means. The control means 4 permits the appropriate sequencing of the various valves of the instant invention. Collectively, the system sequences and times the opening/closing of each valve as well as the sampling device but will allow an operator to program the length of time each valve will remain open. This provides a means by which the process control system can be adapted and incorporated into a variety of different process applications.

Different sized valves, different materials of construction, different process flow temperatures and flow rates different cleaning or chemical agents (steam, air, wash medium, etc.) and other process materials can influence the proper timing of the various facets of operation (sampling, cleaning, sterilizing, resampling, etc.). A single cycle sequence of the basic components of the system of the instant invention will now be discussed.

The control means 4 controls the functioning of the main sample subassembly 2 in tandem with the five peripheral process flow control valves 5, 6, 7, 8 and 9. The control sequencing is laid out in FIGS. 20 and 21. This sequence is designed to clean and sterilize the inlet passage 12, main sample subassembly 2 and drain passage 14 before each sampling. This system will also purge the last of the sampling material into the disposal means 98. After the blunt sealing tip 32 closes orifice 33, the system will also be cleaned and resterilized between each sampling.

The pure steam feed block 5, for example, will control the flow of steam to sterilize the system. Likewise, the pure air feed block 6 will control the flow of pure air through the system for two purposes. First, this air will be blown through the inlet passage 12, sample cavity 11, drain passage 14 and to the disposal means 98 such that any sampling material that might remain after a sampling is removed. This air is also blown down the drain passage 14 such that any steam condensate that remains after the sterilization phase is completely removed. The pure air will both cool and dry the sampling system before the next sample is taken. The wash medium can be provided by the wash medium valve block 7 to clean the system if steam is insufficient. Likewise, a combination of steam and wash medium can be used. The pure dry air 70 can also be used to help flush the wash medium from the system and to dry the system after the use of wash medium.

The drain line block 9 will be open to drain away condensate, wash medium and the like during cleaning and sterilization. The sample vial block 8, on the other hand, will be open to allow the sample material to flow into the sample collector 94.

Figures 20, 21:
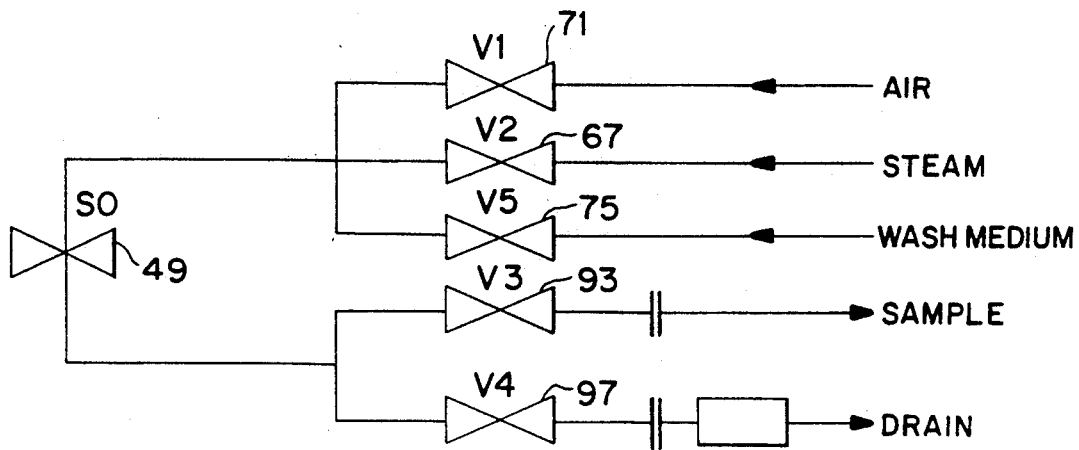
FIG. 20 is a schematic view showing the operation of certain valves in the instant apparatus.
FIG. 21 is an example of a timing chart for one operation of the instant invention.

In FIG. 20, valves 49, 71, 67, 93 and 97 are indicated by S0, V1, V2, V3 and V4, respectively. As indicated in this figure, a waiting period will first be encountered during one type of sampling operation. The valve indicated as V1 and V4 will be open. In other words, the diaphragm pneumatic valves 67 and 97 will be open. Steam will rush from source 66 through inlet passage 12, sample cavity 11 and out drain passage 14 to the disposal means 98 while valve 97 is still open. After an appropriate period of time, the valve 67 will be closed and the valve 71 will be open. Pure dry air can then rush through the system to the disposal means 98. This pure dry air will not only force any remaining particulate matter through the system but will also aid to cool and dry the interior of the apparatus.

In the timing chart of FIG. 21, a one-second delay is then indicated. It should be recognized that this delay could be omitted or could be for a shorter or longer duration. Sampling will next take place. In this arrangement, the valve S0 and V3 are indicated as being open. In other words, the valve 49 will be opened to permit the sample to exit the vessel or conduit 53 through the port 54 thereof. The material will move through orifice 33 into sample cavity 11 and down drain 14 to the sample collector 94. While it is not shown in the FIG. 21 arrangement, it should be noted that the valve 93 can initially be closed and the valve 97 opened such that a first portion of the sample will actually go to the disposal means, if so desired. In any case, valve 97 should close before valve 93 opens.

No valves are provided in the interior of the sample cavity 11 for preventing the sample from entering the inlet passage 12. The valves 67, 71 and 75 will be closed such that an internal pressure will be sufficient to prevent the sample from traveling up inlet passage 12. Moreover, gravity also prevents the sample from traveling up the inlet passage 12. The apparatus A is therefore simplified and can be used in existing vessels or conduits 53 without modification due, in part, to the omission of extra valves. In other words, the relatively small size of body 10 can be maintained such that it is compatible with existing vessel or conduit ports. Moreover, potential sites of contamination are avoided by omitting such additional valves.

After a sufficient sample has been selected at collector 94, another one-second delay is indicated in FIG. 21. Again, no delay or a greater or lesser time period can be provided. The valve 49 indicated by S0 in FIG. 21 is then closed and the valve 71 is opened. Pure dry air will then rush through the system in order force the sample in cavity 11 and drain passage 14 into the sample collector 94. Accordingly, one operation of the apparatus of the instant invention has been described. It should be understood that the wash medium valve block 7 can also be operated if so desired. However, in the arrangement of FIG. 21, the wash medium from source 74 is not used.

As previously noted, the arrangement in FIG. 19 shows the body 10 of the apparatus being inserted into a vessel or conduit 53. When stagnant layers 60 may be present in the vessel, a mounting arrangement shown in FIG. 19 can be used. This design places orifice 33 beyond these stagnant layers 60. The apparatus A used in this design of FIG. 19 is similar to the arrangement of FIG. 2 except two o-ring grooves 35 and 35' are provided on the cap 44 and the length of this cap 44 is greater in FIG. 19. A single o-ring 34 can be moved between the two grooves 35 or 35' as needed. Of course, two separate o-rings could be provided, one for each groove. However, when the apparatus A is positioned as shown in FIG. 19, it is preferred to omit an o-ring from the forward groove 35. In this manner, it is less likely that material would become trapped at the forward, outer end of the cap 44.

It should be appreciated that after the body 10 is mounted in the arrangement of FIG. 19, this body 10 is not movable. Rather, it extends within the vessel or conduit 53 for the predetermined distance indicated during its operation. Of course, when this device is no longer needed, the means 57 for coupling can simply be detached and this apparatus A removed from the vessel or conduit 53. Due to the forward o-ring groove 35, this body 10 can be mounted substantially flush with the wall 61 of the vessel or conduit 53. The o-ring groove 35' with o-ring 34 will form a seal between body 10 and vessel or conduit 53 when the apparatus A is extended as shown in FIG. 19. Alternatively, when the face of cap 44 is generally flush with the interior 61 of vessel or conduit 53, an o-ring in groove 35 will form a seal between the apparatus A and the vessel or conduit 53. The o-ring 34 can be moved from the rearward groove 35' to the forward groove or a new o-ring can be inserted in groove 35 while the rearward groove 35' may or may not retain the o-ring 34.

Up to this point, the instant invention has been discussed as a sampling apparatus. As shown in FIG. 18, this instant invention can also be used as a feed/inoculation means. In FIG. 18, the apparatus A is mounted on the top of vessel 53. When used as a feed/inoculation apparatus, the instant invention can also be mounted on the side of vessel 53.

The feed/inoculation arrangement shown in FIG. 18 is similar to the sampling arrangement previously discussed. However, the drain passage 14 extends well into the sample cavity 11 to prevent pooling of the sample or cleaning material in this arrangement. The opening 48 for drain passage 14 is generally adjacent the wall of cap 44 having orifice 33.

As indicated in FIG. 18, a means 101 is provided for feeding the sample. This means 101 will supply the sample through the inlet passage 12, sample cavity 11, orifice 33 and into the vessel or conduit 53. After the sample has been charged to the orifice or conduit 53, the sealing tip 32 can be moved to close orifice 33. Then the supply means 50 can feed steam, dry air and/or wash medium through the inlet passage 12, sample cavity 11 and out of the drain passage 14 to the means for collecting drain 52.

Indicated schematically in FIG. 18 is a switching means 102 utilized with the supply means 50 and means 101 for feeding sample. This means 102 selects whether the means 101 will supply the sample through the inlet passage 12 or whether the supply means 50 will clean and/or sterilize the inlet passage 12 and other downstream structure.

Apart from having the end 48 of the drain passage 14 located at the end of the sample cavity 11, the diameter of the drain passage 14 is of a sufficiently small diameter such that the pressure in sample cavity (created from inflow through passage 12) will be sufficient to force any material fed through inlet passage 12 up and out drain passage 14. In this manner, the size of the sample fed to the sample cavity 11 is limited by the size of the inlet passage 12. When the supply means 50 is operated, sufficient air, steam, and/or wash medium can be fed through the inlet passage 12 in order to force any sample or other contaminant through the drain passage 14 to the means for collecting 52. Otherwise, the design of the feed/inoculation arrangement shown in FIG. 18 is similar to the sample assembly previously discussed.

The instant apparatus A has several advantages. Its geometry will enable the body 10 and its contents to be relatively small such that it can be retrofitted into existing vessels or conduits. For example, the 25 mm standard size for ferrules 1 can be accommodated with the instant invention.

The instant invention provides a uniquely designed biocompatible, resterilizable flexible diaphragm which allows the sample extraction orifice to be flush mounted with or penetrated into the vessel or conduit 53. A customized subassembly design is possible in which all of the contamination-prone opposing sliding/rotating surfaces are sealed from the sample. For example, the bellows 30 separates and isolates a sample from the operating portions of the valve 49. Other control features such as the steam feed valve block 5, pure dry air valve block 6 and wash medium valve block 7 are removed from the sample. Since contamination-prone parts are removed from the process, the instant apparatus A is a more effective overall sanitary design.

The instant apparatus A is free-draining and will avoid pooling. Pockets between the sample cavity 11 and the drain passage 14 are not present such that pooling or accumulation of a sample or drain is further avoided.

All secondary seals are static to provide the most effective barrier to leakage within the system and/or to the outside environment. Further, the interfaces between the abutting surfaces on the process side (where crevice-related carryover contamination often occurs) are sealed with the static seals (with the exception of the specially designed primary seal which is a diaphragm-type seal).

The instant invention avoids the need for dynamic o-ring seals. Void volume in the sample cavity 11 is minimized. Tortuous flow is also avoided. Therefore, minimal loss of sample material during the sampling process and maximized reproducibility and accuracy of measured samples is had with the instant invention. By using small volumes, only small errors in measurements will be made.

Within this 25 mm outside diameter design discussed, the instant design permits up to six mm outside diameter particles to pass from the vessel or conduit 53 through the sample cavity 11 and out of the drain line 14 to the sample collector 94. Therefore, physical distortion of the sample constituents is avoided, thereby assuring that samples taken are not biased due to size exclusion.

All static threaded connections and abutting surfaces of the instant invention are placed behind static o-ring seals. This removes trouble-prone interfaces from contacts with process flow.

The control means 4 and means for detecting 4a of the instant invention provide for automatic sampling or inoculation. Therefore, operator error is avoided. Manual override also permits sampling even in the case of power failure.

Pressure or temperature profiling of the system and independent indirect verification enables a more reliable operation.

Accordingly, with the instant invention, an accurate subsample of the process composition can be had. This arrangement can be used with existing systems or with new systems. Maintenance of the instant apparatus can easily be carried out Because the body 10 of the instant invention can be machined from a single piece of metal, plastic or other material, if so desired, the need for additional junctures is eliminated. This also avoids potential points for contamination to the sample. Also, the bulb design of the sealing tip 32 avoids dead space.

Due to the control means 4, the timing sequence can easily be changed. For example, an operator can change the length of each of the phases in the sampling process and, using feedback from the temperature and/or sensor probe 19, determine if any error has occurred in the system.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. An apparatus for moving a sample of a flowable material through a port in a wall of a vessel or conduit comprising:
   a body having an end wall and an internal cavity communicable with an orifice formed in said end wall, said body having a generally centrally disposed longitudinal axis extending therethrough;
   a bellows positioned within said internal cavity, said bellows having a tubular body and a sealing tip cooperable with said orifice for opening and closing said orifice, said tubular body being spaced from interior surfaces of said internal cavity to define a sample cavity between said tubular body and said interior surfaces, said sample cavity being communicable with said orifice;
   a valve operating rod extending within said body for reciprocating the sealing tip of the bellows to thereby open and close the orifice;
   a drain passage formed within said body, said drain passage communicating at one end with said sample cavity and extending away from said orifice, the drain passage having a longitudinal axis which is nonparallel, nonperpendicular and offset from the longitudinal axis of the body; and
   an inlet passage formed within said body, said inlet passage communicating at one end with said sample cavity and extending away from said orifice, the inlet passage having a longitudinal axis, a plane passing through the longitudinal axis of the drain passage and the longitudinal axis of the body being nonparallel, nonperpendicular and offset from the longitudinal axis of the inlet passage.

2. The apparatus as recited in claim 1, wherein the body has a generally flat internal wall at the sample cavity and the apparatus further comprises means for preventing accumulation of the sample within the sample cavity, said means for preventing comprising openings of the drain passage and the inlet passage to the sample cavity being positioned for free flow of the sample to avoid accumulation of the sample.

3. The apparatus as recited in claim 2, wherein the sample is supplied through the port to the sample cavity and then through the drain passage such that the apparatus is a sampling apparatus, the apparatus further comprising means for collecting the sample from the drain passage.

4. The apparatus as recited in claim 3, wherein the drain passage and internal wall of the body are generally flush and uninterrupted at the opening of the drain passage to the sample cavity.

5. The apparatus as recited in claim 3, wherein the opening of the inlet passage to the sample cavity is above the opening of the drain passage to the sample cavity.

6. The apparatus as recited in claim 5, wherein the longitudinal axis of the body coupled to the port is generally horizontal, wherein the longitudinal axis of the inlet passage forms an upward angle with a horizontal plane of generally at least 18.5° and wherein the longitudinal axis of the drain passage forms a downward angle with the horizontal plane of generally at least 3°.

7. The apparatus as recited in claim 5, wherein an angle between the inlet passage and the drain passage is a minimum of 21°, the inlet passage and drain passage fail to be horizontal and wherein the drain passage has at least a 3° downward angle with a horizontal plane when the apparatus is attached to the vessel or conduit.

8. The apparatus as recited in claim 5, wherein the body extends upwardly and wherein an angle of the longitudinal axis of the inlet passage with a horizontal plane is greater than an angle of the longitudinal axis of the drain passage with the horizontal plane.

9. The apparatus as recited in claim 1, wherein a generally horizontal plane passes through the longitudinal axis of the body, a first angle being formed between the longitudinal axis of the inlet passage and the generally horizontal plane and a second angle being formed between the longitudinal axis of the drain passage and the generally horizontal plane due to sloping of the inlet and drain passages with respect to the generally horizontal plane.

10. The apparatus as recited in claim 1, wherein an inner diameter of the drain passage is greater than an inner diameter of the inlet passage.

11. The apparatus as recited in claim 1, wherein the body has a generally cylindrical shape with an outer diameter of 25 mm or less.

12. The apparatus as recited in claim 1, wherein the drain passage has an internal diameter of generally 6 mm.

13. The apparatus as recited in claim 1, further comprising means for detecting abnormal operation of the device, the means for detecting comprising a probe with the probe being one of at least a temperature probe and a pressure probe, the probe being located in one of the body and the drain passage.

14. The apparatus as recited in claim 13, further comprising control means for controlling movement of the sealing tip of the bellows by the valve operating rod, the control means further including at least a part of the means for detecting, the control means storing recorded data from the probe and receiving current data from the probe, the data being at least one of temperature information and pressure information, temperature information being received if the probe is a temperature probe and pressure information being received if the probe is a pressure probe, the control means compares current data with recorded data to determine operating changes.

15. The apparatus as recited in claim 1, further comprising supply means operatively connected to the inlet passage, means for collecting sample flow operatively connected to the drain passage and means for collecting drain operatively connected to the drain passage;
the supply means supplying at least one of steam, air and a wash medium to the inlet passage, the sample cavity and the drain passage to thereby flush the inlet passage, sample cavity and drain passage, the sealing tip of the bellows closing the orifice when the supply means is activated;
the means for collecting the sample being closed to the drain passage when the supply means is activated and thereafter is open to the drain passage to receive the sample from the vessel or conduit after the sealing tip opens the orifice; and
the means for collecting drain being open to the drain passage when the supply means is activated and thereafter being optionally closed to the drain passage after the sealing tip opens the orifice, the means for collecting drain receiving the at least one of steam, air and wash supplied from the supply means, through the inlet passage, the sample cavity and the drain passage,
whereby said apparatus is used as a sampling apparatus to receive the sample from the vessel or conduit in the means for collecting while avoiding contamination of the sample due to the supply means and the means for collecting drain.

16. The apparatus as recited in claim 15, wherein the body has a generally flat internal wall at the sample cavity and wherein an opening of the drain passage to the sample cavity is generally flush, uninterrupted and without pockets for accumulation of the sample such that pooling of the sample between the sample cavity and drain passage is avoided.

17. The apparatus as recited in claim 1, wherein the sample is supplied to the port through the inlet passage, and wherein at least one of steam, air and wash medium is supplied to the sample cavity through the inlet passage such that said apparatus is a feed/inoculation apparatus, and the apparatus further comprising means for feeding the sample to the inlet passage.

18. The apparatus as recited in claim 17, further comprising supply means for feeding the at least one of steam, air and wash medium to the inlet passage and comprising control means for controlling movement of the sealing tip of the bellows by the valve operating rod, the control means closing the orifice with the sealing tip when the supply means is activated such that the at least one of steam, air and wash medium is fed through the inlet passage, through the sample cavity and out of the drain passage and wherein the control means opens the orifice when the means for feeding the sample is activated.

19. The apparatus as recited in claim 1, wherein the body is positionable such that the only portion of the apparatus in contact with an interior of the vessel or conduit when the sealing tip of the bellows closes the orifice is a side of the end wall facing the vessel or conduit and the sealing tip.

20. The apparatus as recited in claim 1, wherein the body is positionable as to extend into the vessel or conduit to thereby minimize the effects of stagnant layers within the vessel or conduit adjacent interior surfaces thereof and wherein the body has a plurality of grooves for sealing rings around a periphery thereof.

21. The apparatus as recited in claim 1, wherein the bellows is flexible and encloses the valve operating rod, the bellows having a plurality of folds.

* * * * *